United States Patent [19]

Fujishima et al.

[11] 4,102,803

[45] Jul. 25, 1978

[54] OXYGEN-CONSUMING COMPOSITION

[75] Inventors: Daishiro Fujishima; Shinichiro Fujishima, both of Sagamihara, Japan

[73] Assignee: Mitsubishi Shoji Kaisha, Ltd., Tokyo, Japan

[21] Appl. No.: 736,245

[22] Filed: Oct. 27, 1976

Related U.S. Application Data

[63] Continuation of Ser. No. 524,987, Nov. 18, 1974, abandoned.

[30] Foreign Application Priority Data

Dec. 27, 1973 [JP] Japan .............................. 49-144482
Jan. 7, 1974 [JP] Japan .............................. 49-5177

[51] Int. Cl.$^2$ ..................... C01B 17/66; B01D 53/14
[52] U.S. Cl. ................. 252/188; 252/105; 423/221; 423/231; 423/515
[58] Field of Search ............... 252/188, 105; 423/515, 423/221, 231

[56] References Cited

U.S. PATENT DOCUMENTS

| | | | |
|---|---|---|---|
| 1,736,464 | 11/1929 | Rodman et al. | 252/188 |
| 3,169,068 | 2/1965 | Bloch | 252/188 |
| 3,798,172 | 3/1974 | Etters | 252/188 |
| 3,839,218 | 10/1974 | Owen et al. | 252/188 |

FOREIGN PATENT DOCUMENTS 384,903  12/1932  United Kingdom ................. 423/515

*Primary Examiner*—Benjamin R. Padgett
*Assistant Examiner*—Irwin Gluck
*Attorney, Agent, or Firm*—William J. Daniel

[57] ABSTRACT

An effective oxygen-consuming composition for packages, containers, or other closed spaces, especially containing an article susceptible to oxidative deterioration, comprises a dithionite for reacting with oxygen, sufficient alkaline material to at least partially neutralize sulfur dioxide released as a by-product of the oxygen consuming reaction, and porous filler particles in sufficient amount to promote contact with the ambient atmosphere, all in homogeneous mixture.

11 Claims, No Drawings

OXYGEN-CONSUMING COMPOSITION

This is a continuation of Ser. No. 524,987, filed Nov. 18, 1974, now abandoned.

BACKGROUND OF THE INVENTION

This invention relates to an oxygen-consuming composition for removing oxygen from the air in a closed space by chemical reaction. More specifically, this invention relates to an oxygen-consuming composition which contains a dithionite as the active oxygen-consuming component. In particular, this composition is advantageously used for controlling the storage environment of various articles which are susceptible to oxidative effects, including the propagation of aerobic microorganisms, such as fungi, by providing the composition in a confined container holding the articles to thereby significantly reduce the oxygen content of the interior atmosphere.

It is known that dithionites are capable of reacting with oxygen in the air and thus consuming the oxygen. However, the rate of this reaction is slow and dithionites are thus not well adapted for the purpose of removing oxygen rapidly. Hence, dithionites have not been used as an industrially advantageous anti-oxidant agent.

One of the major problems in storing and transporting articles or products susceptible to oxidative deterioration is how to remove the oxygen from packages for such articles to prevent such deterioration, either directly by oxidation of the products themselves or indirectly as by proliferation of fungi. As is common knowledge, many products lose commercial value through gradual deterioration by the influence of oxygen when left in the open air, irrespective of whether they are of organic or inorganic nature. If an article is easily susceptible to oxidation, it is readily converted into an oxidized product by oxidation with oxygen in the air. Even if the article is fairly resistant to oxidation directly, its commercial value will be lowered by proliferation of aerobic fungi, which grow well in the presence of oxygen.

Among the previous proposals for preventing oxidative deterioration of such articles involves packaging the same in a container of aluminum foil or plastic film with the air in the package being evacuated or replaced by carbon dioxide or nitrogen.

However, such a packaging method requires large scale equipment and is expensive. It also fails to prevent deterioration of the articles by the oxygen which gradually penetrates through the package walls because the aluminum foil or plastic film cannot exclude oxygen completely. Such problems of deterioration of articles during storage, transportation and packaging could be substantially alleviated if a simple and effective means can be provided to remove oxygen from the air present in a closed space, but so far this has proved a difficult goal to achieve in practice.

BRIEF SUMMARY OF THE INVENTION

The prime object of this invention is to provide a new method for effectively removing oxygen from air in a closed space in a simple manner.

Another object of this invention is to provide an oxygen-consuming composition adapted to be placed in a closed space to consume oxygen in the air present in that space.

Still another object of this invention is to provide an oxygen-consuming composition effective for commercial application which contains a dithionite as the oxygen-consuming component.

The other objects, features and advantages of this invention will become more fully apparent from the following description.

DETAILED DESCRIPTION OF THE INVENTION

In accordance with this invention, there is provided a composition possessing oxygen-consuming action which comprises a homogeneous mixture of a porous filler and an alkaline material having a dithionite dispersed therein. This composition rapidly reacts with oxygen in the presence of a small amount of water to chemically bind and thus eliminate such oxygen.

Dithionites used in this invention are represented by the general formula $M_nS_2O_4$ wherein M stands for a metallic ion and n for a number determined by the valency of M. Preferable as the metal M are ions of alkali metals, such as sodium and potassium, and less reactive metals, such as magnesium, zinc and cadmium. Sodium dithionite ($Na_2S_2O_4$) is preferably used. This compound reacts readily with oxygen in the air in the presence of water and is converted into the corresponding metallic sulfate, while evolving sulfur dioxide. Thus, in principle, M can be any metal forming a sulfate although where the products in question are edible, possibly toxic metals are to be obviously avoided.

This concurrent production of sulfur dioxide gas makes handling of dithionites difficult and has hindered their industrial use as an anti-oxidant or the like. According to this invention, this difficulty can be avoided by using the dithionite in admixture with an alkaline material. In such a mixture, sulfur dioxide, produced as a by-product of the reaction between the dithionite and oxygen, is consumed by the alkaline material as the other component of the mixture. Thus, the amount of sulfur dioxide actually released from the mixture to the space is regulated by the amount of the alkaline material.

The chemical reactions occurring during the use of the composition of this invention are believed to proceed in the following manner, using for example sodium dithionite and calcium hydroxide or sodium hydroxide as the active ingredients:

$$Na_2S_2O_4 + O_2 \underset{water}{\rightarrow} Na_2SO_4 + SO_2 \uparrow \qquad (I)$$

$$Ca(OH)_2 + SO_2 \rightarrow CaSO_3 + H_2O \qquad (II)$$

$$2NaOH + O_2 \rightarrow Na_2SO_3 + H_2O \qquad (II')$$

Preferred examples of suitable alkaline materials include caustic alkalis, such as sodium hydroxide, potassium hydroxide, calcium hydroxide, magnesium hydroxide and barium hydroxide, and carbonates, such as sodium carbonate, sodium bicarbonate and calcium carbonate. These compounds are used alone or in a mixture of at least two.

According to this invention, the dithionite and alkaline material are mixed with a porous filler. The porous filler serves not only to increase the bulk of the composition but also to prevent the mixture from hardening and to provide good aeration which promotes contact with the oxygen. In addition, the filler per se possesses good gas-adsorbency and adsorbs sulfur dioxide, other kinds of contaminating gas and bad odors, thus providing a good storage environment for most articles. When dithionite and an alkaline material are mixed in the absence of such porous filler, a mixture with good aeration properties could not be obtained and the resulting mixture undergoes hardening after only a short period of use.

The size of the porous filler is not especially critical and may vary from a fine powder to a relatively coarse grain, ranging from, say, about 0.1 mm up to about 3–4 mm or more. As the degree of aeration and the tendency to hardening of the obtained composition are influenced by the size of the filler, selection of a particular size should be made according to the particular end use. In the invention the size of the filler should preferably be as large as sand, i.e., about 0.2–1 mm, preferably as large as about 0.5–1 mm in average diameter. Specific examples of useful porous fillers include active carbon, silica gel, aluminosilicates, i.e. absorbent earths or clays, and plastic foams, such as polyurethane foam. Most preferably is a particulate active carbon (about 0.5–1 mm in diameter) obtained from sawdust.

In order to prepare the composition of this invention, the alkaline material and the dithionite are mixed first into a homogeneous mixture. Then, the porous filler is added to the mixture and mixed. In this manner a mixture is obtained in which the individual components are homogeneously mixed.

During the preparation of the composition of this invention, it is necessary that all the components are completely dry. The presence of moisture tends to promote a premature reaction between a dithionite and oxygen, interfering seriously with the manipulative steps used in preparing the composition, and consequently should be avoided at this stage. Especially, active carbon has a strong water-adsorbing property and should be heated above 200° C, preferably until is becomes red-hot, prior to mixing it with the other components so as to avoid unintentional introduction of significant amounts of water.

As the amount of alkaline material in the composition of this invention determines the amount of sulfur dioxide released, selection of the amount of the alkaline material is important. According to the results of experimental tests, it has been found that when the amount of the alkaline material is 7 times the stoichiometric amount for reaction with the dithionite a significant amount of sulfur dioxide is still released but increasing the stoichiometric rates of the alkaline compound to 7.5:1 of dithionite lowers the amount of sulfur dioxide released to a very small level, while a ratio exceeding 8:1 inhibits the release of sulfur dioxide almost completely. Accordingly, for obtaining a composition which is easy to handle and is effective to substantially completely absorb the sulfur dioxide, the stoichiometric ratio, i.e. the molar ration adjusted according to the stoichiometry of the particular reaction, of the alkaline material to the dithionite should be above about 8:1 except, of course, when release of some sulfur dioxide can be tolerated.

The filler is used in an amount more than about 20 parts by weight, preferably more than about 50 parts by weight, per 100 parts by weight of the alkaline material. If the amount of the filler is too small, hardening of the mixture may take place. The maximum content of filler is about 90% by weight to avoid excessive dilution of the active constituents.

In a preferred example of the composition of this invention, there is used a mixture of 200–500 parts by weight of porous filler, 100 parts by weight of dithionite and 400–500 parts by weight of alkaline material. Thus, the dithionite should generally be present in a minimum amount of about 5% by weight of the composition, although no hard and fast rule is possible because the circumstances of use, especially the amount of oxygen needing to be consumed, can vary widely, as can the molecular weight of the reactive ingredients.

From reactions I and II, or II', above, it will be apparent that each chemical equivalent of dithionite present will theoretically consume by reaction one chemical equivalent of oxygen gas (= 32 g) and release one chemical equivalent of $SO_2$ gas (= 64 g). Ordinarily, one can at least roughly predict the quantity of oxygen that is likely to be present in a given closed spaced to be protected and thus the weight of composition needed.

Similarly, one chemical equivalent of alkaline material will theoretically consume one chemical equivalent of $SO_2$ gas so that, theoretically speaking, a stoichiometric ratio of 1:1 of dithionite and alkaline material would be expected to suffice for the purposes of this invention. However, as indicated by the previously mentioned results, the neutralization of sulfur dioxide at the stoichiometrically equal level may take long periods of time to reach substantial completion so that a considerable excess of the alkaline material is advantageous to inhibit against the presence of $SO_2$ at any time. A ratio of up to about 20:1 or even higher of alkaline material to dithionite is possible, the upper limit not being critical, but this great an excess would rarely be needed.

The oxygen-consuming composition of this invention is capable of removing oxygen in the air gradually. As the rate of oxygen consumption is markedly accelerated in the presence of water, a small amount of water may be added to the mixture if rapid removal of oxygen is required and sufficient moisture is not al eady present in the article to be packaged or stored. In this case, the use of water in an amount of less than 3% by weight, generally 1 to 2% by weight, of the total mixture is sufficient. In air with high humidity, for example, where the relative humidity is above 70%, there is no particular need for addition of water and many products will contain moisture which will be released into the space to accelerate the oxygen-consuming reaction. As the earlier reaction schemes show, water is a by-product of the reaction, once it is initiated. Alternatively, water can be provided by using a hydrated or crystalline form of alkaline material.

To simplify use, the oxygen-consuming composition of this invention is preferably packed in separate air-permeable bags made of paper or microporous plastics which can be sealed singly or in a group in a virtually airtight container made of an impervious material, such as polyethylene or aluminum foil. The container can then be opened when needed for removal of the bag to be used as such. In this case, the rate of oxygen-consumption of the composition can be controlled by varying the air-permeability of the wrapping of the individual packages, thereby regulating the amount of oxygen which penetrates through the wrapper.

The oxygen-consuming composition of this invention can be used in various fields for the purpose of removing oxygen in a closed space. In particular, the composition of this invention has utility in the fields of packaging and storing of many articles susceptible to propagation of aerobic fungi and/or oxidative deterioration.

Among these articles are clothes or other textile products, optical parts including optical lenses and prisms, various foods, and metallic products such as iron nails and parts of precision instruments for which oxidation causes problems.

According to this invention, deterioration of these articles by oxygen can be prevented by storing or packaging such articles in a closed space in the presence of the present composition. In this case, a standard amount of the composition present should be selected so that it can absorb 2 to 3 times as much oxygen as in the container. If the amount is selected on this basis, the composition will still be active enough to absorb any oxygen which might penetrate the packaging material for the article during storage. According to this invention, the concentration of oxygen in the container can be decreased to and maintained below 1%.

Compositions of this invention containing the alkaline material in a stoichiometric ratio above about 8:1 relative to the dithionite do not permit release of any substantial amount of sulfur dioxide and so are used advantageously for articles susceptible to sulfur dioxide. On the other hand, compositions containing the alkaline material in a ratio less than 8:1, especially 1-3:1 and preferably 1.5-2:1, relative to the dithionite will allow release of sulfur dioxide. Because of the sterilizing effect of sulfur dioxide, this ratio can be used advantageously for foods and the like requiring sterilization. In this case, however, the sulfur dioxide will persist in a closed space only termporarily as it will eventually be absorbed by the alkaline material and the filler and will disappear.

Compositions of this invention containing a carbonate as the alkaline material release an equivalent amount of carbon dioxide instead of water. In this case, reaction II above is expressed by the following equation:

$$SO_2 + Na_2CO_3 \rightarrow Na_2SO_3 + CO_2 \uparrow \qquad (II')$$

Thus, compositions containing an alkaline carbonate have the advantage that the internal pressure of the closed space is not reduced. Therefore, these compositions can be used to remove oxygen in the air from containers which are fragile to external forces such as glass, plastic, etc. On the other hand, the water releasing effect of the hydroxides will not be realized with the carbonates.

The present compositions can be used in bulk, i.e., in loose flowable admixed condition, in which event it is preferably packaged as mentioned above, in convenient quantities in wrappers, pouches, or small cartons of air-permeable material. Alternatively, the containers or packages to be protected could be constructed with an air-permeable compartment for the composition. Also, the mixture can be shaped, as by light pressing, into porous granules, chips, or similar small bodies providing reasonable surface contact with ambient atmosphere.

This invention will be explained in more detail by way of examples. However, it is not intended that the scope of this invention be limited by these examples.

EXAMPLE 1

(A) Preparation of the Oxygen-consuming Composition

3 Grams of sodium dithionite, 12 g of calcium hydroxide and 6 g of active carbon having a diameter of about 1 mm (and referred to hereinafter merely as "active carbon") were mixed homogeneously in a dry state. The mixture was put in a paper bag, and after the addition of 1 g of water, the bag was sealed. The bag was then placed in a polyethylene outer bag and tightly sealed.

(B) Oxygen-consumption Test

The polyethylene outer bag was opened and the paper bag (to which a pH test paper was adhered) containing the composition of this invention was taken out and placed in a polyvinylidene chloride bag of 1000 cc capacity which was then sealed tightly. After a lapse of a certain length of time, the oxygen concentration in the polyvinylidene chloride bag was measured by measurement of the reduction of the amount of the gas in the bag. It was then found that the concentration of oxygen was less than 1.0% by volume. No change was observed in the color of the pH test paper attached to the paper bag and it was confirmed that sulfur dioxide was not present in the space of the polyvinylidene bag.

EXAMPLE 2

A dilute solution of dextrin starch having a concentration of 2% was prepared and two test pieces were made by immersing a cotton cloth in the solution. In a container made of aluminum foil with a capacity of 1000 cc, one of the test pieces was placed and moistened by spraying with water. In this container a paper bag containing the composition described in Example 1 was also placed and the container was tightly sealed. In this case, the free space in the container was 600 cc.

For the purpose of comparison, the other test piece was tested in exactly the same manner except that the composition of this invention was omitted.

The test samples packaged in this manner were kept in a room warmed at 37° C for 30 days and then examined. Development of fungi was not observed on the test piece packaged according to this invention. On the control test piece, however, white fungi developed all over the surface and grey and red fungi were seen here and there.

EXAMPLE 3

Test samples were prepared by immersing iron nails in a 10% brine solution and drying them rapidly.

One handful of these nails was placed in an aluminum foil container with a capacity of 1000 cc. A paper bag containing the composition referred to in Example 1(A) was also inserted and the container was then tightly sealed (Sample AA). In this case the free space in the container was 800 cc.

For the purpose of comparison, another handful of these nails was packaged tightly in exactly the same manner except that the composition of this invention was omitted (Sample BB). The samples AA and BB were stored at normal temperature for 50 days and then examined.

It was observed the the sample AA did not gather rust, whereas the sample BB gathered rust all over the surface of each nail.

EXAMPLE 4

To a dry mixture of 3 g of sodium dithionite, 12 g of calcium hydroxide and 5 g of active carbon were added 2 g of water. The mixture was put in a paper bag. The bag was then placed in an aluminum foil container with a capacity of 1000 cc containing 400 g of coffee (roasted and ground) and the container was tightly sealed (sample AA). In this case the free space in the container was 600 cc.

For the purpose of comparison, coffee (roasted and ground) was sealed in an aluminum foil container in the same manner as described above except that the composition of this invention was omitted (sample BB).

The two aluminum foil containers containing coffee were allowed to stand at room temperature for 2 months. The aluminum foil containers were then opened and the coffee was taken out and examined. As a result, it appears that flavor and taste of the sample AA did not change during storage, whereas the sample BB was changed due to oxidation and its original flavor had deteriorated.

EXAMPLE 5

To a dry mixture of 3 g of sodium dithionite, 12 g of calcium hydroxide and 5 g of active carbon were added 2 g of water. The mixture was put in a paper bag. The bag was then placed in an aluminum foil bag with a capacity of 1000 cc containing 250 g of fried croutons and the bag was tightly sealed (sample AA). In this case, the free space of the bag was 600 cc.

For the purpose of comparison, croutons were put in an aluminum foil bag in the same manner as described above except that the composition of this invention was omitted, and the bag was tightly sealed (sample BB).

The aluminum foil bags containing croutons were allowed to stand at room temperature for 2 months. The aluminum foil bags were then opened and the samples were examined. As a result, it was found that oxidation of the lipid contained in the sample AA was completely inhibited and its color, flavor and taste had not changed during storage. On the other hand, the sample BB was changed due to oxidation of the lipid and had an unpleasant odor.

EXAMPLE 6

3 Grams of sodium dithionite, 2 g of calcium hydroxide and 5 g of active carbon were mixed in a dry state. The mixture was put in a paper bag and 1 g of water was added. The bag was then sealed tightly. When an oxygen-consumption test was performed using this composition in the same manner as described in Example 1 (B), the oxygen concentration in the container was found to be less than 1% by volume. In this case, the color of the pH test paper changed initially to indicate an acidic value of pH 2–3, indicating the release of sulfur dioxide, but returned to original color indicating neutrality within 2–3 hours.

EXAMPLE 7

Four cooked hamburgers each weighing about 60 g were placed in an aluminum foil container with a capacity of 1000 cc. A paper bag containing the composition described in Example 6 was placed in the aluminum foil container and the container was tightly sealed (sample AA). In this case, the free space in the container was about 600 cc.

For the purpose of comparison, four more cooked hamburgers were also sealed in the same manner as described above except that the composition of this invention was omitted (sample BB).

Hamburgers packaged in this manner were placed at 37° C for 7 days. The containers were then opened and examined for proliferation of microorganisms. As a result, microbes were not observed in the sample AA hamburgers packaged with the composition of this invention. The odor was normal and the taste was good.

When water in the sealed container was adsorbed on test paper for detecting sulfur dioxide, no sign was found of the existence of sulfur dioxide.

On the other hand, the sample BB hamburgers emitted a bad odor and it appeared that they were rotten.

Partially cooked hamburgers can be preserved in this same manner.

EXAMPLE 8

A bag with a capacity of 1000 cc made of a nearly air-impervious plastic film was charged with 200 g of bread crumbs. A paper bag containing the composition described in Example 6 was inserted in the bag which was then sealed tightly (sample AA). In this case, the free space in the bag was 600 cc. For the purpose of comparison, bread crumbs were also tightly sealed in the same manner as described above except that the composition of this invention was omitted (sample BB).

Both samples were then allowed to stand at 37° C for 30 days and examined. As a result, no development of fungi was observed in the sample AA bread crumbs. The flavor was maintained and the taste was good.

On the other hand, the sample BB bread crumbs for comparison had a strong septic odor and was completely rotten with propagation of fungi.

Obviously many modifications and variations of the present invention are possible in the light of the above teachings. It is, therefore, to be understood that within the scope of the appended claims, the invention may be practiced otherwise than as specifically described.

What is claimed is:

1. An oxygen-consuming composition comprising a substantially dry homogeneous mixture of a particulate porous gas absorbing filler and an alkaline material having a dithionite uniformly dispersed therethrough, said alkaline material being present in a stoichiometric ratio of at least about 7.5:1 and being selected from the group consisting of alkaline hydroxides and carbonates.

2. The composition of claim 1 wherein said ratio is at least 8:1.

3. The composition according to claim 1 wherein said dithionite is present in an amount of at least about 5% by weight of the composition.

4. The composition according to claim 1 wherein said dithionite is sodium dithionite.

5. The composition according to claim 1 wherein said particulate filler is about 0.1–4 mm in an average diameter.

6. The composition according to claim 1 wherein said alkaline material is an inorganic hydroxide.

7. The composition according to claim 1 wherein at least 20 parts by weight of said particulate filler is present per 100 parts by weight of said alkaline material.

8. The composition according to claim 1 including up to about 3% by weight of water.

9. A composition according to claim 1 wherein said filler is granular active carbon of 0.2–4 mm in average diameter, said alkaline material is selected from calcium hydroxide, magnesium hydroxide, sodium carbonate and sodium bicarbonate, and said dithionite is sodium dithionite.

10. A method for removing oxygen from the air in a closed space by introducing into such space a quantity of the composition according to claim 1 sufficient to consume said oxygen by reaction with said dithionite.

11. A method according to claim 10 wherein said closed space is a closed container or package enclosing an article susceptible to oxidative deterioration.

* * * * *

UNITED STATES PATENT OFFICE
CERTIFICATE OF CORRECTION

Patent No. 4,102,803　　　　　　　　Dated　July 25, 1978

Inventor(s)　Daishiro Fujishima et al

It is certified that error appears in the above-identified patent and that said Letters Patent are hereby corrected as shown below:

In the Heading:

Item [30] Foreign Application Priority Data, "49-144482" should read -- 48-144482 --.

Signed and Sealed this

Sixteenth Day of January 1979

[SEAL]

Attest:

RUTH C. MASON
Attesting Officer

DONALD W. BANNER
Commissioner of Patents and Trademarks